(12) United States Patent
Wolz

(10) Patent No.: US 8,943,693 B2
(45) Date of Patent: Feb. 3, 2015

(54) METHOD FOR PRODUCING TOOTH PARTS FROM DENTAL METAL POWDER

(75) Inventor: Stefan Wolz, Bad Sobernheim (DE)

(73) Assignee: WDT-Wolz-Dental-Technik GmbH, Bad Sobernheim (DE)

( * ) Notice: Subject to any disclaimer, the term of this patent is extended or adjusted under 35 U.S.C. 154(b) by 0 days.

(21) Appl. No.: 13/392,191

(22) PCT Filed: Jul. 30, 2010

(86) PCT No.: PCT/EP2010/061119
§ 371 (c)(1),
(2), (4) Date: Mar. 29, 2012

(87) PCT Pub. No.: WO2011/023490
PCT Pub. Date: Mar. 3, 2011

(65) Prior Publication Data
US 2012/0174404 A1  Jul. 12, 2012

(30) Foreign Application Priority Data

Aug. 27, 2009 (DE) .................. 10 2009 039 102

(51) Int. Cl.
| B23P 13/00 | (2006.01) |
| A61C 13/00 | (2006.01) |
| B22F 3/10 | (2006.01) |
| B22F 3/22 | (2006.01) |
| C22C 1/04 | (2006.01) |
| C22C 19/07 | (2006.01) |
| B22F 1/00 | (2006.01) |

(52) U.S. Cl.
CPC ........... *A61C 13/0003* (2013.01); *B22F 3/1025* (2013.01); *B22F 3/22* (2013.01); *C22C 1/0433* (2013.01); *C22C 19/07* (2013.01); *B22F 2001/0092* (2013.01)
USPC ......... 29/896.11; 29/896.1; 409/131; 419/56; 419/57

(58) Field of Classification Search
CPC ........... A61C 5/10; B21F 43/00; B21F 13/00; B21F 35/00; B23P 13/00; B23P 15/16; B29D 17/00; H04R 31/00; G04D 3/00; A44C 27/00; B23Q 11/00; B23C 3/00
USPC .................... 29/896.1, 896.11; 409/131, 132; 419/56, 57
See application file for complete search history.

(56) References Cited

U.S. PATENT DOCUMENTS

| 4,661,071 A * | 4/1987 | Bell et al. .................. 433/223 |
| 4,937,928 A * | 7/1990 | van der Zel .................. 29/896.1 |
| 5,362,438 A * | 11/1994 | van der Zel ..................... 419/28 |
| 5,697,980 A * | 12/1997 | Otani et al. .................... 424/423 |
| 5,909,612 A * | 6/1999 | van der Zel ........................ 419/5 |
| 5,975,905 A * | 11/1999 | Kim et al. .................. 433/222.1 |
| 6,027,012 A * | 2/2000 | Bes et al. ........................ 228/175 |
| 6,808,659 B2 * | 10/2004 | Schulman et al. ............... 264/16 |
| 7,022,173 B2 * | 4/2006 | Cummings et al. ............. 106/35 |
| 8,813,364 B2 * | 8/2014 | Schechner et al. .......... 29/896.11 |
| 2002/0017021 A1 * | 2/2002 | Panzera ........................ 29/896.1 |
| 2005/0048193 A1 * | 3/2005 | Li et al. ......................... 427/2.24 |
| 2006/0138716 A1 * | 6/2006 | Schluter et al. ................ 264/681 |
| 2006/0168815 A1 * | 8/2006 | Saliger et al. .............. 29/896.11 |
| 2006/0185170 A1 * | 8/2006 | Lewis et al. ................ 29/896.11 |
| 2007/0065780 A1 * | 3/2007 | Dorsman et al. ............... 433/215 |
| 2008/0213119 A1 * | 9/2008 | Wolz ................................ 419/30 |
| 2009/0004630 A1 * | 1/2009 | van der Zel et al. .......... 433/223 |
| 2009/0115084 A1 * | 5/2009 | Moon .............................. 264/16 |
| 2009/0189315 A1 * | 7/2009 | Gunster et al. ................. 264/442 |
| 2009/0252635 A9 * | 10/2009 | Neirinck et al. ................... 419/2 |
| 2009/0321971 A1 * | 12/2009 | Brodkin et al. ................. 264/17 |
| 2010/0041542 A1 * | 2/2010 | Rolf et al. ...................... 501/104 |
| 2010/0316976 A1 * | 12/2010 | Vizanski ........................ 433/219 |
| 2011/0260349 A1 * | 10/2011 | Rolf et al. ........................ 264/16 |
| 2011/0269618 A1 * | 11/2011 | Knapp et al. .................. 501/103 |
| 2012/0193841 A1 * | 8/2012 | Wang et al. .................... 264/645 |
| 2013/0069264 A1 * | 3/2013 | Giordano ........................ 264/16 |
| 2013/0081272 A1 * | 4/2013 | Johnson et al. .............. 29/896.1 |
| 2013/0180110 A1 * | 7/2013 | Schechner et al. ........... 29/896.1 |
| 2013/0236854 A1 * | 9/2013 | McEntire et al. ............. 433/173 |
| 2014/0124991 A1 * | 5/2014 | McEntire et al. ............. 264/626 |

FOREIGN PATENT DOCUMENTS

| EP | 1964629 A2 | 9/2008 |
| JP | H10277061 A | 10/1998 |
| JP | 2006 520221 A | 9/2006 |
| JP | 2008 531841 A | 8/2008 |
| WO | 2008/087214 A1 | 7/2008 |
| WO | 2008/114142 A1 | 9/2008 |

* cited by examiner

Primary Examiner — Essama Omgba
Assistant Examiner — Darrell C Ford
(74) Attorney, Agent, or Firm — Frank H. Foster; Kremblas & Foster

(57) ABSTRACT

The invention relates to a method for producing tooth parts from dental-grade metal powder, wherein existing CAD/CAM milling machines can be used. The essential process steps consist of: a) preparing a slurry from dental-grade metal powder, b) casting the slurry into a mold, c) drawing out (drying) suspension liquid (water) until a mechanically stable blank is obtained, d) milling the blank into the desired shape, e) oxygen-free sintering of the tooth parts milled from the blank. Because the blank is still present as a green body, milling does not place great demands on the milling machine in terms of mechanical stability and dust development. As a result, the operating speed and the service lives of customary milling machines are substantially increased.

9 Claims, No Drawings

METHOD FOR PRODUCING TOOTH PARTS FROM DENTAL METAL POWDER

BACKGROUND OF THE INVENTION

The invention relates to a method for producing tooth parts from dental-grade metal powder. Within the context of the present invention, tooth parts are understood particularly as bridge structures and caps, along with full prostheses.

Prior Art

In the dental industry, the lost-wax casting process continues to be the most commonly used process for producing tooth parts from metal, in which process a wax mold is modeled on a working model, with the shape of said mold corresponding to the object to be cast. Using this wax mold, a cavity is formed in a casting mold, which is then cast with metal. This method is highly costly and requires a great deal of artisanal skill.

For this reason, a number of methods have already been proposed, which are implemented using not molten metal but metal powder which is sintered. None of these methods has gained acceptance in practical use for a wide variety of reasons.

However, one promising method is disclosed in EP 1 885 278 B1 (Wolz). In this case, a metal layer is deposited by electrophoresis from a suspension fluid onto a model, wherein the deposited metal layer is stabilized by sintering, in that it is either fixed on a firing support, or in that it remains on a plated stump, or is placed in a muffle filled with embedding compound or temperature-resistant powder.

In addition to the production of tooth parts from metal, the production of fully ceramic dental prostheses is known, and makes up approximately 10% of the dental market. One customary method consists in using CAD/CAM techniques to mill a framework out of an isostatically pre-pressed block of ceramic, particularly zirconium oxide. In this case, the patient's teeth or a working model is/are scanned, and the framework is milled on the basis of the scanned model. With this method, tooth parts are also milled from solid metal blocks. One major disadvantage of this method is that the milling of ceramic produces dust, and also places high mechanical demands on the milling machine. As a result, the service life of simple, in other words inexpensive, milling machines is too short. Even more complex milling machines, the investment costs of which frequently exceed the economic capability of an average dental laboratory, require an unjustifiable expenditure on maintenance. For these reasons, many dental laboratories no longer even use milling machines.

BRIEF SUMMARY OF THE INVENTION

Statement of the Problem

The invention therefore addresses the problem of allowing the milling machines already existing in dental laboratories to be used to produce tooth parts from metal, the quality of which satisfies all requirements of dental medicine.

Embodiment Example

In what follows, the invention will be specified in greater detail in reference to the production of tooth parts from a CrCo (chromium cobalt)alloy. However, the invention is not restricted to CrCo alloys, and can instead be used with all other non-ferrous alloys and noble metal alloys.

DETAILED DESCRIPTION OF THE INVENTION

The invention starts out with a slurry made of CrCo dental-grade metal powder. In EP 1885 278 B1 (Wolz), the production of a dental-grade metal slurry is described for the first time. An improved CrCo slurry is commercially available under the name WOLCERAM CrCo slurry, which is used here. It consists of 98 wt % CrCo powder and 2 wt % water (suspension liquid) with small admixtures of organic compounds and preservative agents. Before this slurry is used, a conditioning of the slurry is highly recommended, in order to prevent agglomerates. A corresponding device for this purpose is disclosed in German patent DE 10 2005 023 737 B4 (Wolz). After conditioning, a mold made of silicone rubber is filled, in order to produce a round disk having a diameter of 95 mm and a thickness of 20 mm. The slurry is solidified to a usable blank (green body) by drying the slurry in the mold. To ensure that no air bubbles are present in the slurry, it is subjected to pressure treatment at 6 bar, during which air is pressed out of the slurry. This is followed by the drying process, in which the mold is dried in a drying cabinet at 65° C. for 7 hours. Drying can also be carried out under a vacuum and/or under compression. It is recommended to design the base of the mold as having a water-absorbent layer (e.g., blotting paper), so that the water is able to escape not only on the surface but also on the bottom side of the slurry. The resulting concentration gradient of the water concentration is thereby reduced, preventing the non-aqueous auxiliary agents from emerging on the surface. The result of drying is a disk-shaped green body, which corresponds to the shape of the blanks that are processed in customary CAD/CAM milling machines. From the solid blank (green body) approximately 30 tooth parts are milled out of both sides, and remain attached to one another by connectors. Once the connectors have been removed, 30 tooth parts are left. In contrast to milling from a metal disk, with the present method, the removal of the connectors and the smoothing of the connector sites can be easily carried out, since the material is still relatively soft.

The resulting green tooth parts are then subjected to oxygen-free sintering. For this purpose, they are placed in a sintering furnace, such as is disclosed in the older patent application 10 2009 037 737.9 (application date Aug. 17, 2009). The green CrCo tooth parts are sintered at 1190° C. for a period of 45 min. To expel the oxygen, 2.5 l/min argon is introduced. The sintering results in metallic, shiny tooth parts made of CrCo metal, which can still be faced, as is customary. Of course, the shrinkage that occurs as a result of sintering must be compensated for by means of a corresponding CAM/CAD program.

The sintered product has the following properties. The chemical composition has been determined via emission spectroscopy.

| Co % | residual | Mn % | <1.0 | Cr % | 28.0-30.0 |
|---|---|---|---|---|---|
| Si % | <1.0 | Mo % | 5.0-6.0 | Fe—C—Ni | traces <0.5% |

Technical data: Density (g/cm$^3$) 8.3 average linear WAK 25-500° C. ($10^{-6}$ K$^{-1}$)' 14.5 E-modulus (GPa) 228.7 0.2% offset yield strength (MPa) 817 strain at break (%) 9.7 Vickers hardness (HV5/30) 375 chemical solubility μg/cm$^2$<4

Standards: ISO 9693:1999; ISO 22674:2006; ISO 10993-5:1999

Because some milling machines operate using water as their coolant, it can be problematic that the raw material is still water soluble. Once the blank has been tempered at 250-400° C. or 250 to 500° C. for 2 to 3 hours, however, the material can be milled in the presence of water without problems. The material is then stable in an aqueous environment.

The invention claimed is:

1. A method for producing tooth parts having a desired shape from dental-grade metal powder, characterized by the process steps:
   a) preparing a slip of dental-grade metal alloy powder, consisting of chromium cobalt (CrCo) alloy, with a suspension liquid and an admixture of organic compounds,
   b) pouring this slip into a mold,
   c) drawing the suspension liquid out of the poured slip to produce a reduced concentration gradient such that the resulting concentration gradient of the suspension liquid prevents the admixture of organic compounds from emerging on a surface of the slip until a mechanically stable green blank is obtained,
   d) following step c) and before step e), milling the green blank to the desired shape, and
   e) oxygen-free sintering the tooth parts that have been milled from the green blank, including expelling oxygen by introduction of argon into a sintering furnace.

2. The method according to claim 1, characterized in that the suspension liquid is water, and the water is drawn out from the surface by drying inside a silicon mold.

3. The method according to claim 2, characterized in that the suspension liquid is also drawn out at the base of the mold by way of a water-adsorbent layer thereby reducing the resulting concentration gradient.

4. The method according to claim 2 characterized in that the step of drawing suspension liquid out is carried out under applying vacuum or pressure to the cast slip.

5. The method according to claim 2, characterized in that said drying is realized in a drying cabinet.

6. The method according to claim 5 wherein water solubility of the blank is avoided by tempering the blank at 250 to 500° C.

7. The method according to claim 1, characterized in that water solubility of the green blank is avoided by tempering the green blank at 250 to 500° C.

8. The method according to claim 1 characterized in that, before the step of drawing suspension liquid out, the slip is subjected to pressure during which air is pressed out of the slip.

9. The method according to claim 1, wherein the blank is disk-shaped in order to be machinable by customary CAD/CAM milling machines.

* * * * *